United States Patent [19]

Kuu

[11] Patent Number: 4,832,690

[45] Date of Patent: May 23, 1989

[54] NEEDLE-PIERCEABLE CARTRIDGE FOR DRUG DELIVERY

[75] Inventor: Wei-Youh Kuu, Vernon Hills, Ill.

[73] Assignee: Baxter International Inc., Deerfield, Ill.

[21] Appl. No.: 6,525

[22] Filed: Jan. 23, 1987

[51] Int. Cl.⁴ .............................................. A61M 5/14
[52] U.S. Cl. ...................................... 604/85; 604/83; 604/56; 604/92
[58] Field of Search ............................ 604/56, 82–92, 604/410, 411, 414, 415, 416, 892

[56] References Cited

U.S. PATENT DOCUMENTS

| | | |
|---|---|---|
| 2,811,156 | 10/1957 | Bragg .................................. 604/84 |
| 3,732,865 | 5/1973 | Higuchi et al. . |
| 4,034,756 | 7/1977 | Higuchi et al. . |
| 4,034,758 | 7/1977 | Theeuwes . |
| 4,036,227 | 7/1977 | Zaffaroni et al. . |
| 4,077,407 | 3/1978 | Theeuwes et al. . |
| 4,111,202 | 9/1978 | Theeuwes . |
| 4,279,362 | 7/1981 | Pursell ................................. 604/83 |
| 4,298,003 | 11/1981 | Theeuwes et al. . |
| 4,410,321 | 10/1983 | Pearson et al. . |
| 4,411,662 | 10/1983 | Pearson . |
| 4,424,056 | 1/1984 | Urquhart et al. ................... 604/85 |
| 4,432,755 | 2/1984 | Pearson . |
| 4,432,756 | 2/1984 | Urquhart et al. . |
| 4,439,183 | 3/1984 | Theeuwes . |
| 4,458,733 | 7/1984 | Lyons . |
| 4,465,471 | 8/1984 | Harris et al. . |
| 4,474,574 | 10/1984 | Wolfe et al. . |
| 4,479,793 | 10/1984 | Urquhart et al. . |
| 4,479,794 | 10/1984 | Urquhart et al. . |
| 4,484,909 | 11/1984 | Urquhart et al. . |
| 4,511,352 | 4/1985 | Theeuwes et al. ................... 604/85 |
| 4,511,353 | 4/1985 | Theeuwes et al. ................... 604/85 |
| 4,515,585 | 5/1985 | Urquhart et al. ................... 604/85 |
| 4,525,162 | 6/1985 | Urquhart et al. . |
| 4,533,348 | 8/1985 | Wolf et al. .......................... 604/85 |
| 4,534,757 | 8/1985 | Geller . |
| 4,534,758 | 8/1985 | Akers et al. ........................ 604/85 |
| 4,548,599 | 10/1985 | Urquhart et al. . |
| 4,552,555 | 11/1985 | Theeuwes . |
| 4,573,967 | 3/1986 | Hargrove et al. ................... 604/85 |
| 4,581,014 | 4/1986 | Millerd et al. . |
| 4,586,922 | 5/1986 | Theeuwes et al. ................... 604/85 |
| 4,664,650 | 5/1987 | Urquhart et al. ................... 604/85 |

FOREIGN PATENT DOCUMENTS

| | | | |
|---|---|---|---|
| 59694 | 9/1982 | European Pat. Off. ............. 604/84 |
| 86/03417 | 6/1986 | PCT Int'l Appl. .................. 604/82 |

Primary Examiner—Stephen C. Pellegrino
Assistant Examiner—Ralph Lewis
Attorney, Agent, or Firm—Paul C. Flattery; George H. Gerstman; Bradford R. L. Price

[57] ABSTRACT

A needle-pierceable cartridge for drug delivery comprises a housing containing a drug-containing bag having wallls of hydrophilic material capable of diffusing water across the walls, whereby osmosis can take place. The bag walls also define macroscopic holes, so that water on the outside of the bag diffuses by osmosis into the bag, and osmotic pressure forces water containing dissolved drug out of the bag through the macroscopic holes for removal and use.

24 Claims, 2 Drawing Sheets

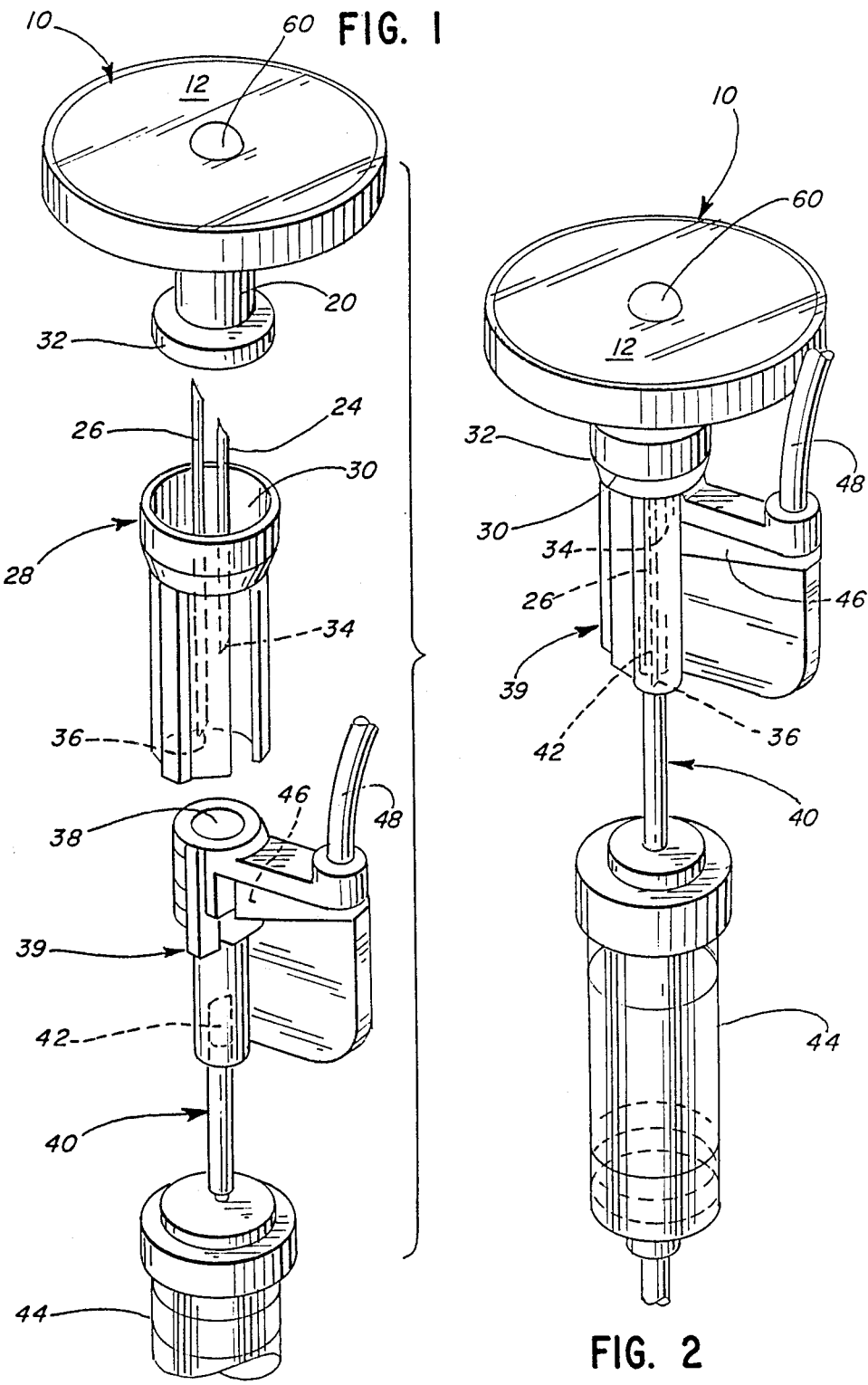

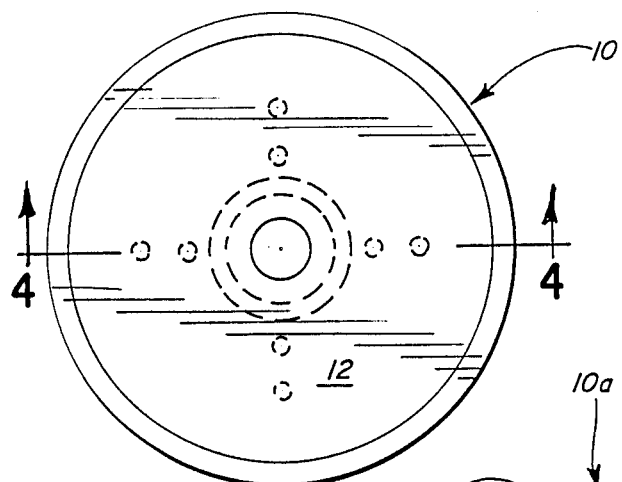
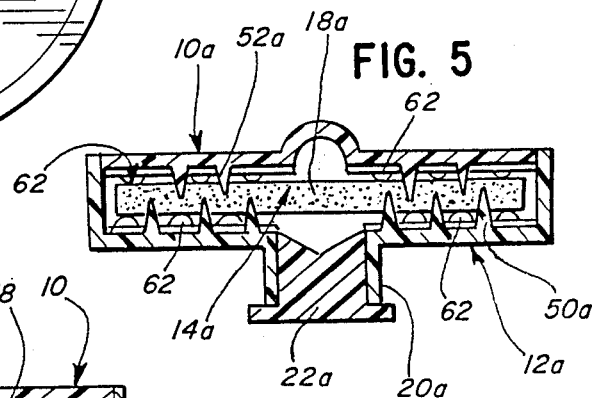
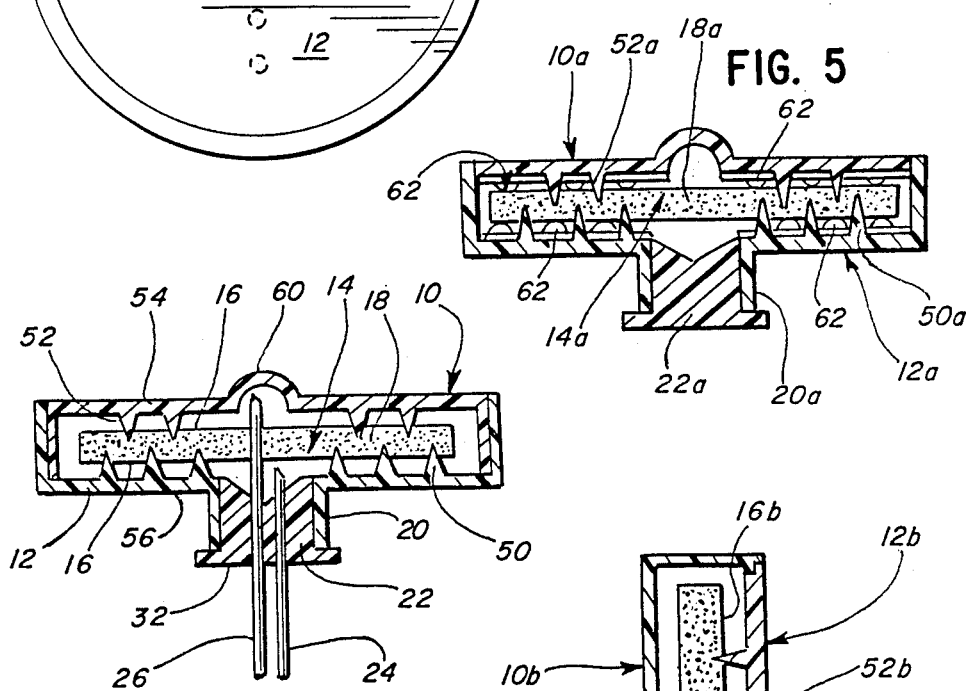
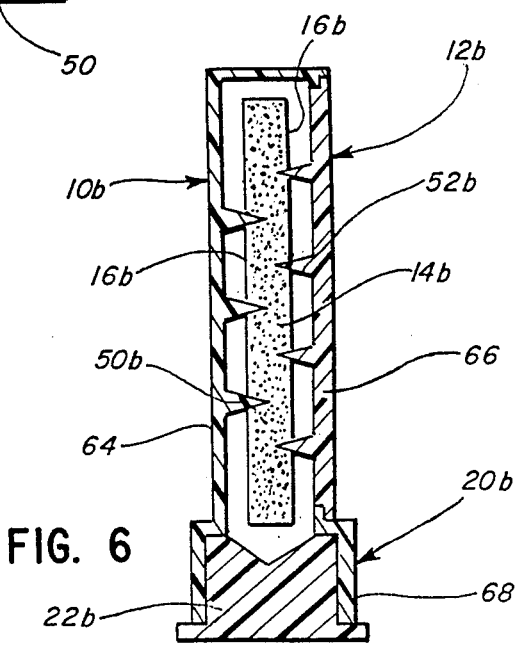

NEEDLE-PIERCEABLE CARTRIDGE FOR DRUG DELIVERY

BACKGROUND OF THE INVENTION

The present invention relates to the typically intravenous delivery of a drug to a patient in convenient, safe, and effective manner, while typically providing improved uniformity of drug dosage over the entire delivery cycle.

Many drugs are mixed with a diluent before being delivered intravenously to a patient. The diluent may be, for example, a dextrose solution, a saline solution, or water. Many such drugs are supplied in powder form and packaged in glass vials or ampules. Other drugs, such as used in chemotherapy, may be packaged in glass vials or ampules in a liquid state.

Powdered drugs may be reconstituted in a well-known manner, utilizing a syringe which is used to inject liquid into the vial for mixing, the syringe then withdrawing the mixed solution from the vial. When a drug must be diluted before delivery to a patient, the drug is often injected into a container of diluent after if is reconstituted, which container may be connected to an administration set for delivery to a patient. More specifically, the diluent may be packaged in glass bottles or flexible plastic containers. These containers may have administration ports for connection to an administration set, which delivers the container contents from the container to the patient. The drug is typically added to the container through an injection site on the container.

Drugs may be packaged separately from the diluent for various reasons. One of the most important reasons is that many drugs do not retain their chemical and physical stability when mixed with the diluent, and thus cannot be stored that way for any substantial period of time. Also, drugs are often packaged separately from the diluent because many firms which manufacture drugs are not engaged in the business of providing medical fluids in containers for intravenous delivery, and vice versa.

Therefore, a doctor, nurse, pharmacist or other medical person must mix the drug and diluent, often making use of a needle and syringe. This presents a number of problems. The reconstitution procedure is time consuming and requires aseptic technique. the operator must provide the proper diluent and a syringe before beginning. Often the powdered drug is "caked" at the bottom of the vial. Thus, when liquid is injected into the vial from a syringe the surface area of contact between the liquid and the powdered drug may be quite small initially, thus making the mixing procedure even more time consuming.

Also, because of the limited vial volume, the increasing drug concentration in the diluent makes it harder to finish the reconstitution process. The operator may attempt to solve this by repeatedly injecting solution into the vial, mixing and withdrawing the solution, but this makes necessary additional injections and movement of the syringe, which increase the likelihood of contamination. Also, it is sometimes difficult to get all of the drug and/or liquid out of the vial, thus increasing the time required to perform the reconstitution procedure.

The above reconstitution procedures should be performed under preferably sterile conditions, which are expensive, time consuming, and aften hard to maintain. In some instances, a laminar flow hood may be required under which the reconstitution procedure is performed.

After a drug is reconstituted and withdrawn into a syringe barrel, the drug may in some instances be injected immediately into the intravenous system of a patient. More typically however, the reconstituted drug is injected from the syringe into a larger container of solution as discussed above, for connection to an intravenous administration set. This is because often the drug reconstituted in the syringe is still at a concentration so high as to cause local toxicity in the veins of a patient near the injection site where the needle pierces the skin. This may create severe vein irritation which may be medically harmful.

Additionally, even though the proper dose of medication is in the syringe, immediate injection into the patient's blood stream may create a condition of systemic toxicity wherein the level of drug concentration in the patient's entire blood stream is dangerously high. Yet another reason for not making the injection from the syringe directly into the patient is that it creates an additional injection site into the patient, which may be painful for the patient and which provides another opportunity for infection.

For these reasons, the reconstituted drug is more typically injected into a diluent container.

A patient may typically be administered a dextrose or saline solution from a large volume parenteral container, for example, such as a one liter container, delivered through an administration set such as a CONTINU-FLO administration set sold by Travenol Laboratories. If the reconstituted drug were injected into the large volume parenteral container, delivery of the drug would usually be delivered over too long a time period. Often, these large volume fluids are delivered at very slow flow rates.

Otherwise, the reconstituted drug is injected into a small volume parenteral container, such as a fifty milliliter flexible bag sold by Travenol Laboratories. This container is hung at a higher elevation than the large volume parenteral container and is connected by a secondary administration set to an injection site on the primary administration set. Because it is maintained at a higher elevation, the reconstituted drug in the small volume container is delivered, after which fluid from the large volume container begins to flow once more. By utilizing a small volume container connected to an administration set for delivery of the drug or other beneficial agent instead of a direct syringe injection, the drug is delivered over a preferred time period that tends to minimize negative side effects.

For greater convenience, and to reduce transfers where loss of sterility is possible, closed reconstitution delivery systems are proposed in U.S. Pat. Nos. 4,410,321; 4,411,662; 4,432,755; and 4,458,733, all assigned to Baxter Travenol Laboratories Inc., the assignee of the present invention. As shown therein, containers include a drug and a diluent in separate compartments which are reconstituted in a closed system before the drug is delivered to the patient. Typically, the container is connected to an administration set which is connected at its other end to the primary administration set, such as with the small volume parenteral container described above. The containers shown in these patents solve many of the problems associated with syringe reconstitution. The product does, however, necessitate a series of reconstitution steps which must be performed by the nurse or other operator prior to delivering the fluid from the container.

Delivery of a drug or other beneficial agent in a manner not requiring reconstitution steps by an operator is shown in U.S. Pat. Nos. 4,424,056; 4,432,756; 4,439,183; 4,474,574; 4,479,793, 4,479,794; 4,525,162 and 4,548,599 and Canadian Pat. No. 1,173,795, assigned to Alza Corporation of Palo Alto, Calif. As disclosed in those patents, a parenteral delivery system is disclosed which has a formulation chamber therein for administering a beneficial agent such as a drug. The system is advantageous in that it provides for reconstitution of the drug by fluid flowing from a large volume parenteral container for example, through the administration set containing the formulation chamber with the drug therein. Such systems attempt to eliminate the need for the time consuming reconstitution procedure described above.

Another passive reconstitution system is disclosed in European Patent Application No. 0059694 to Aktiebolaget Hassle of Sweden.

Still another device for delivering a drug "inline", i.e., in the administration set, is disclosed in U.S. Pat. No. 4,534,757 assigned to Alza Corporation. The device holds the drug and includes a section through which the liquid passes in a direction substantially opposite to the general direction in which liquid flows to the patient.

Yet another system which attempts to provide for drug reconstitution in-line without manual reconstitution by a nurse or other operator is shown in U.S. Pat. No. 4,465,471, assigned to Eli Lilly and Co. of Indianapolis, Ind. That patent discloses constructions for a receptacle in the administration set itself. A separate cartridge containing the drug to be reconstituted and delivered to the patient is plugged into the receptacle. As liquid enters the cartridge for reconstitution of the drug and subsequent delivery out of the cartridge and receptacle and into the patient, some or most fluid continues to flow through the administration set, bypassing the cartridge entirely.

European Patent Application Publication No. 0146310 to Eli Lilly and Co. is directed to a system for drug reconstitution including an intravenous administration set and a drug vial, and utilizes the vial vacuum to reconstitute the drug.

U.S. Pat. No. 4,534,758 to Akers et al. discloses a relatively complex drug delivery apparatus with various valves. When liquid from a container is delivered to the drug vial, the vial is to be agitated for a time sufficient to suspend the previously dry medicine.

U.S. Pat. No. 4,581,014 to Millerd et al. assigned to Ivac Corporation of San Diego, Calif. discloses a selector valve for delivering a previously reconstituted drug from a drug vial through an intravenous administration set to a patient.

All the publications described above are directed to attempted solutions to the time consuming reconstitution procedure and/or its associated problems, such as delivery of the solution to a patient. In most of the offered solutions, delivery of the drug is intended to be passive, i.e., once the drug is placed into the administration set, manual reconstitution steps are not required.

Still another common feature of many of the attempted solutions disclosed in these publications is that delivery of the drug is intended to be able to be made in a manner which is essentially independent of the fluid flow rate through the administration set and into the patient. Stated differently, some of the systems are designed to deliver a certain dosage of drug in a prese-lected time period, within a broad range of fluid flow rates. Delivery of a drug independent of flow rate is desirable because it ensures that the necessary dosage will be delivered within a therapeutically acceptable time period, which may be typically about twenty to thirty minutes, although this time period may vary, depending upon the drug and dosage.

By making delivery of the drug or other beneficial agent independent of the flow rate, the system ensures that the drug will not be delivered too quickly should the flow rate be set too high by the nurse or other operator, thereby preventing the problem of systemic toxicity discussed above.

Some of the prior art, such as U.S. Pat. Nos. 4,424,056; 4,479,793; and 4,479,794, are also directed to systems having a beneficial agent placed "in-line" in an administration set for mixing of the agent and delivery to a patient, wherein the delivery of the agent may be made in a given volume of fluid. Also, a valve controlling fluid flow may be manually operated to deliver the agent in a manner which can be made dependent upon fluid flow.

At least the automatic reconstitution type systems discussed above, (i.e., those not requiring a separate agitation or mixing step), suffer from the possibility of creating a concentration of beneficial agent in the fluid being delivered to the patient which is too high at low flow rates. This results in local toxicity to the patient near the point of introduction into the body. The problem is solved by the invention disclosed in U.S. patent application Ser. No. 721,999, filed Dec. 3, 1984, entitled "Drug Delivery Apparatus Preventing Local and Systemic Toxicity", Thomas E. Needham et al., assigned to the assignee of the present invention. Further solutions to the problems of passively mixing and delivering a beneficial agent to a patient are disclosed in U.S. patent application Ser. No. 721,991 filed Dec. 3, 1984 entitled "Housing Enabling Passive Mixing of a Beneficial Agent with a Diluent", Brian Zdeb et al., also assigned to the assignee of the present invention. In that application there is disclosed certain housing constructions for delivering the beneficial agent to the patient. Typically, the housing includes a receptacle which is placed in-line in a medical liquid administration set and a separate cartridge including the beneficial agent. The cartridge is plugged into the receptacle when it is desired to deliver the beneficial agent to the patient. Active reconstitution by a nurse or other operator is not required. Instead, once the cartridge is plugged into the receptacle, liquid flowing from the source of medical liquid through the administration set flows into the receptacle and the agent-containing cartridge, reconstituting the agent. The solution with agent therein flows out the receptacle, down the administration set to the patient's venous system.

A need, however, still remains in the extensive prior art of systems for reconstituting drugs and the like under field conditions for improvements in the uniformity of dosage of the drug in early portions of solutions passed into the system and to the patient, when compared with later portions. It is of course generally desirable that the concentration of reconstituted drug in each c.c. of solution to be administered should be substantially the same as the concentration in other portions of the solution which are to be administered.

By this invention, improvements in the uniformity of concentration of such reconstituted drug solutions for administration can be achieved. At the same time, the dry drug may be stored in a simple, inexpensive cartridge, which is initially separate from an administration set connected to the patient. Thus, cartridges containing different drugs and in variable dosages may be provided, and applied to a conventional solution administration set, for reconstitution for the typically dry drug and administration of the resulting drug-containing solution of improved uniformity of concentration to the patient.

DESCRIPTION OF THE INVENTION

In accordance with this invention, a needle-pierceable cartridge for drug delivery to a patient may be provided, in which the cartridge may be connected to a solution administration set in any desired manner for convenient, uniform reconstitution of the drug within the cartridge, as solution is administered through the set to the patient.

The cartridge of this invention comprises a housing, and a drug-containing bag positioned within said housing, said bag having walls of hydrophilic material capable of diffusing the desired solvent such as water across said walls, whereby osmosis can take place between the drug in the bag and water outside of the bag. Needle-pierceable sealing means are carried by the housing.

The walls of the bag define a plurality of macroscopic holes, so that a needle may penetrate the sealing means to provide water to the exterior of the bag in the housing. Thus, as osmosis takes place through the walls of hydrophilic material, water containing dissolved drug is forced from the bag through the holes for transfer to the patient.

One significant aspect of the operation of the invention as described above relates to the fact that, when osmosis takes place across a membrane because the area on one side of the membrane contains a higher concentration of solute than the area on the other side of the membrane, a positive osmotic pressure will tend to develop on the membrane side containing the higher solute concentration. In this present instance, the dry drug in the bag occupies the side of the osmotic membrane where the solute concentration has the potential for being higher. Thus, an increased osmotic pressure begins to develop inside of the drug-containing bag when i.v. solution or other solution containing no more than physiological concentrations of solutes are provided to the exterior of the bag. However, in this instance, because of the presence of the macroscopic holes in the bag, only a small osmotic pressure can develop within the bag. Instead, solution containing dissolved drug is, in effect, pumped out of the macroscopic bag holes, to be received and conveyed out of the system, carrying the reconstituted drug with it.

Accordingly, the reconstitution of drug in accordance with the invention can take place in a very smooth, uniform, and spontaneous manner, making use of osmotic principles, without need for agitation of the bag or the like. It is generally preferable for the inlet of fresh solution to the bag area to be positioned remotely from the outlet of drug-contianing solution, so that a large amount of the solution passing through the system enters into the osmotic process, passing through the bag wall and then being expelled by the osmotic pressure out of the macroscopic holes.

The needle-pierceable sealing means described above may be of sufficient size to receive two spaced, hollow needles typically of differing lengths, one to provide the water to the outside of the bag, and one to receive the water which contains dissolved drug.

The cartridge also may define inwardly projecting spikes which penetrate the bag to form the macroscopic holes described above. The spikes may penetrate the bag during manufacture of the cartridge, and constitute a convenient manufacturing means to form the holes in a predetermined size and distribution.

The cartridge of this invention may be of a generally disc shape, with the needle-pierceable sealing means being positioned at the center of one side of the disc-shaped housing. In such a circumstance, the housing may define a dome for receiving a needle tip, which typically may pass directly through the bag, with the dome being positioned at the center of the other side of the housing in a manner which is opposed to the needle-pierceable sealing means.

Alternatively, the housing may be of a generally elongated shape, with the needle-pierceable sealing means positioned on one end of the housing. When a pair of needles passes through the needle-pierceable sealing means, they may be of unequal length, with the longer needle extending entirely through the bag and out the other side, and the other needle terminating short of the bag, to provide a good circulation pattern for i.v. solution or diluent within the cartridge.

Additionally, means may be provided for pressing the bag into generally flat configuration, to minimize open, drug-free volume therein. This insures that subtantially all of the disolved drug is expressed out of the bag. This can also improve the circulation pattern through the bag.

The hydrophilic material of which the bag walls are made may be of any material capable of providing the desired osmosis. A large number of such materials are commercially available. For example, cellulose-based dialysis membrane material may be used, with flow control of the cartridge being achieved in part by selection of membrane thickness, type, and size and shape of the holes formed by the inwardly projecting spikes described above, or by other means.

The spikes themselves may be relatively uniformly distributed over the bag area to form uniform distribution of holes. Alternatively, the spikes may be congregated at a area of the bag which is remote from the inlet from the fresh solution, to reduce the amount of fresh solution which shunts around the bag to the outlet, rather than passing through it.

The device of this invention shortens the time required to fully reconstitute its contents into solution for rapid delivery of dry drugs to a patient. Its use is particularly desirable for drugs which are relatively unstable after reconstitution. Additionally, the solution of this invention is particularly desirable for use in administering high molecular weight drugs, since the drug material itself does not have to diffuse through any membrane wall, but is driven from the bag through the macroscopic holes. For example, peptides may be distributed in good uniformity of dosage by this invention, and specifically insulin.

It is to be understood that the term "drugs" should be interpreted in a broad sense. The invention is capable of reconstituting any kind of material which is capable of reconstitution into a solvent, which solvent is typically water. However, the invention may be used as well for other purposes as well, where a non-aqueous solvent reconstitutes other materials which may or may not be pharmaceutical in nature, such processes being equivalents to what is specifically disclosed herein.

The term "macroscopic holes" simply implies a hole which is large enough to be not substantially influenced by osmotic effect in its flow characteristics. Osmosis itself arguably utilizes molecular sized pores extending through the membrane, but while such pores exhibit strong osmotic behavior, holes on the order of 0.001 inch and larger are macroscopic in nature, and are not strongly influenced by osmotic principles. Thus the invention of this application can take advantage of the seemingly contradictory situation where solvent flows through the membrane walls into the bag through the molecular pores, and simultaneously flows out of the bag through the macroscopic pores.

Preferably, at least about 80% of the i.v. or other solution which passes through the bag of this invention diffuses by osmosis through the bag walls to pick up dissolved drug and to pass out of the bag through the macroscopic holes. There is no upper limit to the size of the macroscopic holes except for obvious constraints, i.e. the holes should not be so large that the drug tends to fall out. The holes that are shown in the specific embodiment of this application are actually generally ring-shaped since they constitute a little torn portion of the membrane surrounding each spike. Alternatively, the holes may be of other cross-sections, for example, the membrane holes that would be produced by spikes of L-shaped, Y-shaped, or X-shaped cross sections.

Additionally, the macroscopic holes may be formed in the bag walls prior to placing of the bag into the housing during manufacture, so that spikes are not used.

DESCRIPTION OF THE DRAWINGS

Referring to the drawings,

FIG. 1 is a perspective view of a needle-pierceable cartridge of this invention in exploded relation, showing a portion of an i.v. infusion set and a connection adaptor.

FIG. 2 is a perspective view of the parts of FIG. 1 in their connected relation.

FIG. 3 is a top plan view of the cartridge of FIG. 2.

FIG. 4 is a sectional view taken along 4—4 of FIG. 3.

FIG. 5 is a sectional view, similar to FIG. 4, of a modified embodiment of the cartridge of this invention.

FIG. 6 is a longitudinal sectional view of another modified embodiment of the cartridge of this invention.

DESCRIPTION OF SPECIFIC EMBODIMENTS

Referring to FIGS. 1-4, needle-pierceable cartridge 10 is shown, comprising a housing 12, and a drug-containing bag 14 shown to be generally circular in configuration in the specific embodiment. Bag 14, which is shown schematically, has walls 16 and contains a typically dry material 18. Walls 14 may be made, for example, of Cuprophan cellulose membrane, and may be sealed together in any desired manner. For example, a length of tubular cellulose membrane may be filled with dry drug and sealed at its ends by mechanical means.

Needle-pierceable sealing means constitutes a tubular port 20 in which is carried a rubber plug 22 of conventional design, to permit the sealing access of a pair of hollow needles 24, 26, of differing lengths as shown. When cartridge 10 is in use, needles 24, 26 pass through rubber plug 22 of the sealing means in the manner shown, where the longer needle 26 passes entirely through bag 14 and out the other side, while needle 24 terminates short of the bag.

Needles 24, 26 may be part of adaptor 28 which is of a design as disclosed in Brian D. Zdeb U.S. application Ser. No. 868,827, filed May 29, 1986 entitled Passive Drug Delivery System. Needles 24, 26 are carried in sealing surface 30, which can abut in sealing manner against surface 32 of plug 22. At the same time, the inner ends 34, 36 of needles 24, 26 can penetrate elastomeric sealing site 38 of an i.v. administration set 40. The lower end 36 of longer needle 26 passes through elastomeric sealing tube 42, penetrating out of its lower end for flow communication with drip chamber 44. At the same time, the lower end 34 of shorter needle 24 enters chamber 46, which is in flow communication with upper portion 48 of set 40. Accordingly, liquid flowing down set 40 has no place to go except upwardly through needle 24 into cartridge 10. Solution is withdrawn from cartridge 10 through needle 26, with needle 26 passing through seal 42 into drip chamber 44. Seal 42 prevents solution from flowing downwardly around needle 26.

Cartridge 10 defines a plurality of upper and lower spikes 50, 52 for defining the macroscopic holes in the membrane walls 16 of bag 14. If desired, lower spikes 50 may be dispensed with, to reduce the flow of fresh solution from needle 24 which passes into bag 14 by non-osmotic means, so that the solution which flows out of needle 26 has a higher percentage of liquid that has passed in osmotic manner through the walls 16 of the bag.

Housing 10, as shown, may comprise a pair of shells 54, 56 (FIG. 4) which fit together to form housing 10, and which may be sealed in conventional manner, for example, solvent sealing or radio frequency welding. As the two shells 54, 56 are put together, the respective spikes 50, 52 penetrate the walls of bag 14 as shown.

Thus, i.v. solution, driven, for example, by a gravity pressure head of solution in an elevated container, can pass through tubing 48 into connection site 39 while cartridge 10 is in sealing connection thereto as shown in FIG. 2. The i.v. solution is driven upwardly through needle 24 into housing 10 as shown in FIG. 4. There, the principles of osmosis cause a flow of solvent from the exterior of bag 14 to its interior, where the solvent picks up dissolved drug 18. Osmotic pressure causes solvent, carrying dissolved drug, to pass out of the holes formed by the spikes, to be picked up by needle 26, the tip of which resides within dome 60, which is positioned at the center of the other side of housing 10 from the side which carries needle-pierceable sealing means 20, 22. Thus, reconstituted drug solution passes down needle 26, through sealing member 42, and into drip chamber 44, for administration to the patient.

By this technique, as stated above, the drug can be delivered in very uniform concentration from beginning to end of the reconstitution process. The exact flow characteristics of the cartridge of this invention, and the rate of drug pick-up in the cartridge, can be controlled by such factors as the distribution, size, and shape of spikes 50, 52, the dimensions of housing 10 and bag 14, and the nature and thickness of the hydrophilic bag walls 16.

Turning to FIG. 5, a modified design of cartridge 10a is disclosed. As before, cartridge 10a has a housing 12a of generally similar shape to prior housing 12, and in general the structure and function of cartridge 10a is similar to that of cartridge 10 except as otherwise described herein.

Needle-pierceable sealing means 20aa, 22a is of similar design to the previous embodiment, as are spikes 50a, 52a, and bag 14a.

As a modification, a series of filler members 62 are provided for pressing bag 14a into generally flat configuration, to minimize open, solid drug-free volume therein. By this means, more efficient pick-up of drug material 18a may be provided to solution which enters the interior of bag 14a.

Turning to FIG. 6, a third embodiment of cartridge 10b is disclosed in which housing 12b is of generally elongated shape, and needle-pierceable sealing means 20b, 22b is positioned at one end of elongated housing 12b. In this instance, a pair of needles similar to needles 24, 26 can pass through sealable plug 22b, with the longer needle extending through the entire length of bag 14b and out the upper end thereof, while the shorter needle terminates short of contact with bag 14b.

Spikes 50b, 52b penetrate the hydrophilic membrane walls 16b. The structure and function of this third embodiment may be similar to that of the previous embodiments, except as otherwise specifically described herein.

Housing 12b is shown to be made of three connected parts in this particular instance, namely members 64, 66, and 68, which may be sealed together by any conventional means, for example, solvent sealing or radio frequency welding.

The cartridge of this invention is particularly useful for the administration of very small quantities of drugs or the like, with the hydrophilic bag within the cartridge having a volume capacity of no more than typically 1 c.c. of volume, most of which is filled with a drug material. However, the device of this invention may be used in conjunction with larger volume bags as well.

The above has been offered for illustrative purposes only, and is not intended to limit the scope of the invention of this application, which is as defined in the claims below.

That which is claimed is:

1. A needle-pierceable cartridge for drug delivery to a patient which comprises:

a housing; a drug-containing bag positioned within said housing, means within said housing for supporting said bag, said bag having walls of hydrophilic material capable of diffusing liquid outside of the bag, the walls of said bag defining a plurality of macroscopic holes; and needle-pierceable sealing means carried by said housing, so that a needle may penetrate said sealing means to provide liquid to the exterior of said bag in the housing whereby, as osmosis takes place, liquid containing dissolved drug is forced from said bag through said macroscopic holes for delivery to a site of use.

2. The cartridge of claim 1 in which said needle-pierceable sealing means is of sufficient size to receive two, spaced, hollow needles of differing length, one to provide said water and one to receive said water containing dissolved drug.

3. The cartridge of claim 1 in which said housing is of a generally disk shape, the needle-pierceable sealing means being positioned at the center of one side of said disk-shaped housing.

4. The cartridge of claim 3 in which said housing defines a dome for receiving a needle tip, said dome being positioned at the center of the other side of said housing.

5. The cartridge of claim 1, in combination with a pair of hollow needles of differing lengths penetrating said needle-pierceable sealing means, whereby the needle tips are respectively positioned adjacent opposed walls of said housing exterior to said bag, one needle communicating with a source of said liquid and the other needle communicating with means for receiving said liquid having drug from said bag dissolved therein.

6. The cartridge of claim 5 in which one needle extends entirely through said bag and the other needle terminates short of said bag.

7. A needle-pierceable cartridge for drug delivery to a patient, which comprises:

a housing; a drug-containing bag positioned within said housing, means within said housing for supporting said bag, said bag having walls of hydrophilic material capable of diffusing liquid across said walls whereby osmosis can take place between the drug in the bag and liquid outside the bag, the walls of said bag defining a plurality of macroscopic holes; needle-pierceable sealing means carried by said housing, said needle-pierceable sealing means being of sufficient size to receive two, spaced, hollow needles of differing length; said support means including inwardly-projecting spikes which penetrate said bag walls to form said plurality of macroscopic holes, whereby said two, spaced hollow needles may penetrate the sealing means to provide liquid to the exterior of said bag in the housing through one of said needles so that, as osmosis takes place, liquid containing dissolved drug is forced from said bag through said macroscopic holes and out of the other of said needles for delivery to a site of use.

8. The cartridge of claim 7 in which said housing is of a generally disc-shape, the needle-pierceable sealing means being positioned at the center of one side of said disc-shaped housing.

9. The cartridge of claim 8 in which said housing defines a dome for receiving the needle tip, said dome being positioned at the center of the other side of said housing.

10. The cartridge of claim 7, in combination with the pair of hollow needles of differing lengths penetrating said needle-pierceable sealing means, whereby the needle tips are respectively positioned adjacent opposed walls of said housing exterior to said bag, one needle communicating with a source of said liquid, and the other needle communicating with means for receiving said liquid having drug from said bag dissolved therein.

11. The cartridge of claim 10 in which one needle extends entirely through said bag and the other needle terminates short of said bag.

12. The cartridge of claim 11 in which said housing is of a generally disc shape, the needle-pierceable sealing means being positioned at the center of one side of said disc-shaped housing.

13. The cartridge of claim 7, in which said spikes are uniformly distributed over the bag area to form uniform distribution of macroscopic holes.

14. A needle-pierceable cartridge for drug delivery to a patient which comprises:

a housing; a drug-containing bag positioned within said housing, means within said housing for supporting said bag, said bag having walls of hydrophilic material capable of diffusing liquid across said walls whereby osmosis can take place between the drug in the bag and the liquid outside of the bag, the walls of said bag defining a plurality of macroscopic holes; said support means including inwardly projecting spikes which penetrate said bag to form said holes; and needle-pierceable sealing means carried by said housing, so that a needle may penetrate said sealing means to provide liquid to the exterior of said bag in the housing whereby, as osmosis takes place, liquid containing dissolved drug is forced from said bag through said macroscopic holes for delivery to a site of use.

15. A needle-pierceable cartridge for drug delivery to a patient, which comprises:

a housing; a drug-containing bag positioned within said housing, means within said housing for supporting said bag, said bag having walls of hydrophilic material capable of diffusing liquid across said walls whereby osmosis can take place between the drug in the bag and liquid outside of the bag, the walls of said bag defining a plurality of macroscopic holes; and needle-pierceable sealing means carried by said housing, said housing being of a generally disc-shape, the needle-pierceable sealing means being positioned at the center of one side of said disc-shaped housing, said housing defining a dome for receiving a needle tip, said dome being positioned at the center of the other side of said housing; whereby a needle may penetrate said sealing means to provide liquid to the exterior of said bag in the housing whereby, as osmosis takes place, liquid containing dissolved drug is forced from said bag through said macroscopic holes for delivery to a site of use.

16. The cartridge of claim 14 in which said inwardly projecting spikes are uniformly distributed over the bag area to form uniform distribution of macroscopic holes.

17. The cartridge of claim 1 in which said housing is of a generally elongated shape, the needle-pierceable sealing means being positioned on one end of said housing.

18. The cartridge of claim 1 in which means are provided for pressing said bag into generally flat configuration to minimize open, drug-free volume therein.

19. The cartridge of claim 7 in which said housing is of generally elongated shape, the needle-pierceable sealing means being positioned on one end of said housing.

20. The cartridge of claim 12 in which means are provided for pressing said bag into generally flat configuration to minimize open, drug-free volume therein.

21. The cartridge of claim 7 in which means are provided for pressing said bag into generally flat configuration to minimize open, drug-free volume therein.

22. A needle-pierceable cartridge for drug delivery to the patient which comprises:

a housing, a drug-containing bag positioned within said housing, means within said housing for supporting said bag, said bag having walls of hydrophilic material capable of diffusing liquid across said walls, whereby osmosis can take place between the drug in the bag and liquid outside of the bag; and needle-pierceable sealing means carried by said housing, said sealing means being of sufficient size to receive two, spaced hollow needles of differing length, the walls of said bag defining a plurality of macroscopic holes so that a needle may penetrate said sealing means to provide liquid to the exterior of said bag in the housing, so that, as osmosis takes place, liquid containing dissolved drug is forced from said bag through said macroscopic holes for delivery to a site of use, and means provided for pressing said bag into generally flat configuration to minimize open, drug-free volume therein.

23. The cartridge of claim 22, in combination with a pair of hollow needles of differing length penetrating said needle-pierceable sealing means, whereby the needle tips are respectively positioned adjacent opposed walls of said housing exterior to said bag, one needle communicating with a source of aqueous drug diluent solution and the other needle communicating with means for receiving diluent solution having drug from said bag dissolved therein.

24. The cartridge of claim 22 in which one needle extends entirely through said bag and the other needle terminates short of said bag.

* * * * *